United States Patent [19]

Smiley

[11] Patent Number: 4,841,092

[45] Date of Patent: Jun. 20, 1989

[54] PREPARATION OF TRIS(2-CYANOETHYL)AMINE

[75] Inventor: Robert A. Smiley, Wilmington, Del.

[73] Assignee: E. I. Du Pont De Nemours and Company, Wilmington, Del.

[21] Appl. No.: 197,152

[22] Filed: May 23, 1988

[51] Int. Cl.$^4$ ............................................ C07C 121/43
[52] U.S. Cl. .................................................... 558/455
[58] Field of Search ......................................... 558/455

[56] References Cited

U.S. PATENT DOCUMENTS 2,816,129 12/1957 Montgomery ...................... 558/455
3,409,666 11/1968 Foreman .......................... 558/455 X
4,552,705 11/1985 Tsou et al. ......................... 558/455

Primary Examiner—Joseph Paul Brust

[57] ABSTRACT

A process for the production of tris(2-cyanoethyl)amine from acrylonitrile by reacting acrylonitrile with an ammonium salt dissolved in water at a pH of less than 7.

3 Claims, No Drawings

PREPARATION OF TRIS(2-CYANOETHYL)AMINE

FIELD OF THE INVENTION

This invention relates to an improved process for the preparation of tris(2-cyanoethyl)amine from acrylonitrile in high yield.

BACKGROUND OF THE INVENTION

The production of tris(2-cyanoethyl)amine, hereinafter sometimes referred to as "T-2CEA", from acrylonitrile is the subject of U.S. Pat. Nos. 2,816,129, and 4,552,705. The former patent carries out the reaction in aqueous methanol, in the presence of ammonium acetate. The yield obtained is stated to be about 30%. The latter patent carries out the reaction in a polar solvent at a very large ratio of polar solvent to ammonia.

SUMMARY OF THE INVENTION

The present invention is a process for the production of T-2CEA in high yield and in which the reaction product requires little purification. The process comprises reacting a mixture consisting essentially of acrylonitrile, an ammonium salt of a lower aliphatic acid, water and a lower aliphatic acid at a temperature of 20° to 105° C. The amount of the lower aliphatic acid should be sufficient that the pH of the initial mixture is less than 7. After reaction, the product is precipitated by adding alkali metal hydroxide to the reaction mixture to increase the pH to 11 or higher.

Normally the amounts of acrylonitrile and ammonium salt are selected such that their ratio is in the range of about 0.5 to 3. Normally the amount of water present in the reaction mixture is at least about ⅓ of the total weight of the mixture.

The time required for the reaction is temperature dependent but usually varies from about 2 to 20 hours.

DETAILED DESCRIPTION AND EXAMPLES

In order to achieve the desired product in high yields in a reasonable reaction time, the initial pH of the reaction mixture should be less than 7. This may be achieved by adding a lower aliphatic acid to the mixture. Suitable lower aliphatic acid are those having 1 to 6 carbon atoms, i.e. formic through hexanoic acid, and branched acids such as ethyl methyl acetic acid. Substituted acids such as hydroxyacetic acid and sulfoacetic could also be used. The preferred acid is acetic acid.

The ammonium salt of a lower aliphatic acid can be the salt of any of the acids listed above. Usually the salt employed would be the salt of the acid that is used to bring the pH to less than 7. Ammonium acetate is the preferred salt.

The reaction may be carried out at atmospheric pressure in a reflux reactor, or may be carried out at super atmospheric pressures in a closed reactor.

Following the reaction the pH of mixture is adjusted by the addition of sufficient amount of an alkali metal hydroxide to precipitates the product. The product may be separated by filtration from the other components. The amount of alkali metal hydroxide added normally raises the pH to 11 or higher.

EXAMPLE I 154 g of ammonium acetate (2 moles), 106 grams of acrylonitrile (2 moles), 300 ml of water and 5 ml of acetic acid were combined and placed in a reflux reactor. For about 20 hours the mixture was stirred and heated from an initial temperature of 70° C. to 104° C. The cloudy product mixture was cooled in an ice bath to 20° C. and about 20 ml of 50% sodium hydroxide was added with stirring. A solid precipitated. The solid was filtered off. The product on the filter weighed 94 g. This product was subjected to infra-red and mass spectral analysis and determined to be tris(2-cyanoethyl)amine. The product was recrystallized from ethanol and dried under vacuum to give 62 g of a white solid which has a melting point of 53° to 54° C. The yield was about 53% of theoretical.

EXAMPLE II 453 grams of 30% ammonium hydroxide in 833 ml of water were combined with 500 g of acetic acid. 528 ml (about 8 moles) of acrylonitrile were added to the mixture and the mixture was refluxed until the temperature rose from the initial temperature of 73° C. to 104° C. The mixture was cooled to room temperature, and 100 ml of 50% sodium hydroxide was added with cooling and stirring. A solid product precipitated and was filtered and dried. The yield was 290 g or about 63% of the theoretical yield.

EXAMPLE III 97.5 lb. of deionized water and 55.0 lb. of acetic acid were charged to a 50 gal stirred jacketed kettle. With cooling water circulating in the jacket, 50 lb of conc. ammonium hydroxide was added slowly at such a rate that the temperature was maintained at less than 40° C. Then 46.5 lb. of acrylonitrile was added to the kettle and heat applied until a gentle reflex was obtained at 73° C. Gentle heating was continued for 18 hrs. during which time the reflex temperature increased to 104° C. The kettle contents were then cooled to ambient temperature and discharged into a 60 gal. stirred jacketed tank. With cooling water supplied to the jacket, 24 lb. of 50% sodium hydroxide was added with stirring while keeping the reaction solution below 25° C. After all the sodium hydroxide was added, the tank contents were cooled to below 15° C. with circulating ice-water in the jacket and stirring maintained overnight. The next day, the solid which had formed was filtered off, washed once with deionized water and dried in a vacuum oven at 50° C. The yield of 99.5% pure T-2CEA was 39 lb. or 71.7% of the theoretical.

I claim:

1. A process for the production of tris(2-cyanoethyl)amine which comprises (a) reacting at a temperature of 70° C. to 105° C. a mixture consisting essentially of acrylonitrile, water, an ammonium salt of aliphatic acid having 1 to 6 carbon atoms or hydroxy acetic acid or sulfoacetic acid, and a sufficient amount of an aliphatic acid having 1 to 6 carbon atoms or hydroxyacetic acid or sulfoacetic acid to give the mixture an initial pH of less than 7, and then (b) adding sufficient alkali metal hydroxide to raise the pH to 11 or higher, to precipitate tris(2-cyanoethyl)amine.

2. The process of claim 1 in which the mole ratio of acrylonitrile to ammonium salt is in the range of about 0.5 to 3 and in which water is present in the amount of at least about ⅓ of the weight of the total components present, and in which the reaction time is in the range of about 2 to about 20 hours.

3. The process of claim 1 in which the aliphatic acid is acetic acid.

* * * * *